United States Patent
Mayer (10) Patent No.: US 9,489,615 B2
(45) Date of Patent: Nov. 8, 2016

(54) COUNTING MECHANISM FOR A DRUG DELIVERY DEVICE AND DRUG DELIVERY DEVICE

(71) Applicant: Sanofi SA, Vernier (CH)

(72) Inventor: Stefan Mayer, Freiburg Im Breisgau (DE)

(73) Assignee: Sanofi SA, Vernier (CH)

( * ) Notice: Subject to any disclaimer, the term of this patent is extended or adjusted under 35 U.S.C. 154(b) by 7 days.

(21) Appl. No.: 14/395,803

(22) PCT Filed: May 2, 2013

(86) PCT No.: PCT/EP2013/059178
§ 371 (c)(1),
(2) Date: Oct. 20, 2014

(87) PCT Pub. No.: WO2013/164419
PCT Pub. Date: Nov. 7, 2013

(65) Prior Publication Data
US 2015/0129652 A1    May 14, 2015

(30) Foreign Application Priority Data
May 4, 2012    (EP) ..................... 12166880

(51) Int. Cl.
| | | |
|---|---|---|
| *G06M 1/08* | (2006.01) | |
| *G06M 1/14* | (2006.01) | |
| *G06M 1/16* | (2006.01) | |
| *G06M 3/02* | (2006.01) | |
| *A61M 15/00* | (2006.01) | |
| *G06M 1/22* | (2006.01) | |

(Continued)

(52) U.S. Cl.
CPC ......... *G06M 1/083* (2013.01); *A61M 5/31526* (2013.01); *A61M 15/0065* (2013.01);
(Continued)

(58) Field of Classification Search
CPC ........ G06M 1/083; G06M 1/14; G06M 1/16; G06M 3/02; G06M 1/22; A61M 15/0065; A61M 15/0091; A61M 15/0076; A61M 15/0081; A61M 15/0073; A61M 5/31526; A61M 5/31568; A61M 2005/3126; A61M 2202/064; A61M 15/025
See application file for complete search history.

(56) References Cited

U.S. PATENT DOCUMENTS 5,564,414 A * 10/1996 Walker .............. A61M 15/0065
                                                    128/200.23
7,100,530 B2 * 9/2006 Lu ....................... A61M 15/009
                                                    116/284

(Continued)

FOREIGN PATENT DOCUMENTS

| CN | 1684731 A | 10/2005 |
| CN | 1871044 A | 11/2006 |

(Continued)

*Primary Examiner* — Kristy A Haupt
(74) *Attorney, Agent, or Firm* — McDonnell Boehnen Hulbert & Berghoff LLP (57) ABSTRACT

The present disclosure concerns a counting mechanism for a drug delivery device, comprising a first counting member comprising an interaction element, a second counting member comprising engagement elements that are configured to engage with the interaction element of the first counting member, and a separating member, wherein the first counting member is moveable relative to the separating member between a first and a second relative position, and the separating member is configured to prevent an engagement of the interaction element with the engagement elements when the first counting member is in the second relative position with respect to the separating member. Further, the present disclosure concerns a drug delivery device comprising said counting mechanism.

14 Claims, 5 Drawing Sheets

(51) Int. Cl.
*A61M 5/315* (2006.01)
*A61M 5/31* (2006.01)

(52) U.S. Cl.
CPC ..... *A61M15/0073* (2014.02); *A61M 15/0076* (2014.02); *A61M 15/0081* (2014.02); *A61M 15/0091* (2013.01); *G06M 1/14* (2013.01); *G06M 1/16* (2013.01); *G06M 1/22* (2013.01); *G06M 3/02* (2013.01); *A61M 5/31568* (2013.01); *A61M 15/0025* (2014.02); *A61M 2005/3126* (2013.01); *A61M 2202/064* (2013.01)

(56) References Cited

U.S. PATENT DOCUMENTS

| | | | |
|---|---|---|---|
| 8,573,204 | B2 | 11/2013 | Von Schuckmann et al. |
| 8,833,365 | B2 | 9/2014 | Mayer et al. |
| 2005/0017020 | A1* | 1/2005 | Eckert ............... G06M 1/041 222/30 |
| 2010/0258120 | A1* | 10/2010 | Colomb ............ A61M 15/0045 128/203.21 |
| 2010/0263665 | A1* | 10/2010 | Brown ............. A61M 15/0065 128/203.12 |

FOREIGN PATENT DOCUMENTS

| | | |
|---|---|---|
| CN | 102317958 A | 1/2012 |
| DE | 80366 | 9/1894 |
| DE | 102007056263 A1 | 5/2009 |
| EP | 0684047 A2 | 11/1995 |
| EP | 2201977 A1 | 6/2010 |
| GB | 170833 | 3/1922 |
| WO | 97/20589 A1 | 6/1997 |
| WO | WO 2004/026380 A2 | 4/2004 |
| WO | 2008079350 A2 | 4/2008 |
| WO | 2009065707 A1 | 3/2009 |

\* cited by examiner

Fig. 5

COUNTING MECHANISM FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. §371 of International Application No. PCT/EP2013/059178 filed May 2, 2013, which claims priority to European Patent Application No. 12166880.0 filed May 4, 2012 and U.S. Provisional Application No. 61/750,381 filed Jan. 9, 2013. The entire disclosure contents of these applications are herewith incorporated by reference into the present application.

FIELD OF INVENTION

This disclosure relates to a dose counting mechanism for a drug delivery device and to a drug delivery device comprising such a dose counting mechanism. The drug delivery device may be an inhaler, in particular a dry powder inhaler. However, the dose counting mechanism is also suitable for any other drug delivery device, e.g. an injector such as an injection pen. In particular, the dose counting mechanism may be used in a fixed-dose drug delivery device, i.e. a device in which the size of the drug which is delivered may not be varied by the user. Rather, in a fixed-dose device, the size of the dose is set by the design of the delivery mechanism.

BACKGROUND

It is an object of the present disclosure to provide an improved dose counting mechanism for a drug delivery device, e.g. a small and reliable dose counting mechanism. Furthermore, it is an object of the present disclosure to provide an improved drug delivery device.

This object may, inter alia, be achieved by the subject of the independent claim. Advantageous embodiments and refinements are the subject-matter of the dependent claims. However, further advantageous concepts may be disclosed herein besides the ones which are claimed.

SUMMARY

One aspect relates to a dose counting mechanism for a drug delivery device comprising a first counting member. The first counting member comprises an interaction element. Further, the dose counting mechanism comprises a second counting member which comprises engagement elements that are configured to engage with the interaction element of the first counting member. Moreover, the dose counting mechanism comprises a separating member. Furthermore, the first counting member is moveable relative to the separating member between a first and a second relative position. The separating member is configured to prevent an engagement of the interaction element with the engagement elements when the first counting member is in the second relative position with respect to the separating member.

The interaction element may be a protrusion projecting away from a main body of the interaction element. In particular, the interaction element may be a cam. The engagement elements may be projections, in particular teeth.

The first counting member may be moveable to more than two pre-defined relative position with respect to the separating member. In particular, the first counting member may be moveable to ten pre-defined relative position with respect to the separating member. However, the separating member may be configured to prevent an engagement of the interaction element with the engagement elements in all positions except when the first counting member is in one pre-defined relative position with respect to the separating member. In other words, an engagement of the interaction element and the engagement elements is possible in exactly one of the pre-defined relative positions. This position is referred to as the first relative position in the following. The other nine positions are referred to as second positions.

In particular, the engagement of the interaction element and the engagement elements may correspond to an abutment of said elements. The engagement of the interaction element and the engagement elements may correspond to the interaction element being enabled to directly exert a force on one of the engagement elements. Particularly, when engaged to one of the engagement elements, the interaction element may be enabled to transfer a movement of the first counting member to the second counting member.

By an engagement of the interaction element with the engagement elements, the first counting member is enabled to move the second counting member. Accordingly, the counting mechanism does not require additional parts like separate gearing elements to transfer a movement of one counting member into a movement of the other counting member. Accordingly, the counting mechanism is composed of a small number of components, thereby reducing the space requirements and the costs of the mechanism. In particular, the number of components of the counting mechanism may be given by 2×N−1, wherein N is the number of counting members. The number of counting members is expediently given by the number of digits which should be displayed.

Further, the separating member may be stationary. Accordingly, the separating member may be fixed to a housing of the drug delivery device such that it is not movable relative to said housing.

In one embodiment, the separating member is configured to enable an engagement of the interaction element with one of the engagement elements when the first counting member is in the first relative position with respect to the separating member.

When the interaction element is engaged to the engagement elements, a movement of the first counting member from its first relative position with respect to the separating member to its second relative position may be transferred to the second counting member.

In one embodiment, the first counting member is moveable relative to the second counting member when the first counting member is in the second relative position with respect to the separating member. In other words, the first counting member is moveable relative to the second counting member when the interaction element is not engaged with the engagement elements.

In one embodiment, a movement of the second counting member is triggered by a movement of the first counting member when the interaction element is engaged with the engagement elements.

The movement of the first counting member may in particular be a rotation. The movement of the second counting member may in particular also be a rotation. A movement of the first counting member may correspond to an update of a units digit of a counted number. A movement of the second counting member may correspond to an update of a tens digit of a counted number. The movement of the first and/or the second counting member may correspond to an incrementing or a decrementing of a counted number, preferably by one.

In one embodiment, the interaction element is elastically deformable. In particular, the interaction element has an elasticity such that it is deformed elastically in the second relative position. In this position it may be e.g. bent by an abutment to the separating member. However, at the same time, the elasticity and/or the shape of the interaction element is preferably chosen such that it does not deform significantly when in engagement with the engagement elements. Instead, the interaction element is configured to exert a force on the engagement elements when the first counting member moves from its first relative position to its second relative position.

In one embodiment, the first counting member is rotatable around a first rotation axis relative to the separating member.

Accordingly, the movement of the first counting member from its first relative position to its second relative position is a rotation around the first rotation axis.

In one embodiment, the second counting member is rotatable around a second rotation axis relative to the separating member. The second rotation axis may run along the first rotation axis. In particular, the second rotation axis may be parallel or identical to the first rotation axis. In this case, the first and the second counting member may be co-axial.

Accordingly, when the movement of the first counting member from its first relative position to its second relative position is transferred to the second counting member, said movement of the second counting member is a rotation around the second rotation axis. The first and the second counting member may be configured to rotate into the same rotation direction.

In one embodiment, the separating member comprises a wall provided with an opening. The wall may be arranged in a plane perpendicular to the first rotation axis. The wall may be continuous, except for the opening provided in the wall. The wall may extend around the first rotation axis.

The wall may have a C-shape, particularly as seen in the plane perpendicular to the first rotation axis.

In case the first counting member comprises multiple interaction elements one opening may be provided in the wall for each interaction element. A first counting member comprising multiple interaction elements may, in particular, allow transferring a force to the second counting member in a well-balanced fashion.

In one embodiment, the second relative position of the first counting member with respect to the separating member corresponds to the interaction element being aligned with the wall, e.g. abutting the wall. In other words, the wall may separate the interaction element from the engagement elements when the first counting member is in its second position.

Accordingly, the wall may prevent an engagement of the interaction element of the first counting member with the engagement elements of the second counting member.

In one embodiment, the first relative position of the first counting member with respect to the separating member corresponds to the interaction element being aligned with the opening, e.g. the interaction member may protrude through the opening. This alignment may be an alignment as seen in a direction perpendicular to the first rotation axis.

Accordingly, in the first relative position, the opening allows an engagement of the interaction element of the first counting member with the engagement elements of the second counting member. In other words, the separating member allows an interaction of the first and the second counting member only, if the first counting member or its interaction element is in a defined relative position with respect to the opening.

In one embodiment, the first counting member comprises a first main body comprising the interaction element, the first main body is arranged adjacent to the wall of the separating member on a first side of the wall, the second counting member comprises a second main body comprising the engagement elements, and the second main body is arranged adjacent to the wall of the separating member on a second side of the wall opposite to the first side. In other words, the wall is arranged between the interaction element and the engagement elements.

In particular, the first main body, the second main body and the wall may have a tubular or cylindrical shape. The first main body, the second main body and the wall may differ in their respective radius. The first main body may be arranged outside the wall and the second main body may be arranged inside the wall, preferably as seen in a plane perpendicular to the first rotation axis. Alternative, the first main body may be arranged inside the wall and the second main body may be arranged outside the wall, preferably as seen in a plane perpendicular to the first rotation axis.

In one embodiment, one of the first and the second main body is arranged inside the other one of the first and the second main body. Thereby, the wall may be arranged between the first and the second main body. This arrangement may, in particular, be given in a plane perpendicular to the first rotation axis.

In particular, the interaction element protrudes through the opening in the wall in the first relative position of the first counting member with respect to the separating member.

In one embodiment, the interaction element abuts the wall in the second relative position of the first counting member with respect to the separating member.

In particular, the interaction element may be elastically deformed due to the abutment with the wall.

In one embodiment, the first counting member is rotatable in a first rotational direction around the first rotation axis, and the interaction element projects from a sidewall of the first counting member, wherein the interaction element and the sidewall define an acute angle. The acute angle may be defined in a direction opposite to the first rotational direction, preferably as seen in a plane perpendicular to the first rotation axis.

The acute angle facilitates an elastic deformation of the interaction element when the first counting member is moved from its first relative position with respect to the separation member to its second relative position. Further, the acute angle is chosen such that a movement of the first counting member is transferred to the second counting member when the interaction element is engaged to one of the engagement elements.

In one embodiment, the first counting member comprises a first index element, the second counting member comprises a second index element, and the first and the second index element are configured to cooperate to display a number.

Each of the index elements may comprise digits. Each of the index elements may follow every movement, i.e. every rotation, of the corresponding main body. Accordingly, a movement of one of the counting members may correspond to an update of the counted number, i.e. an incrementing or a decrementing of the counted number.

The counted number may correspond to the number of doses left in the device. Alternatively, the counted number may correspond to the number of drug delivery operations that has been carried out.

The first index element may display the units digit of the counted number. The second index element may display the tens digit of the counted number. In case the counted number corresponds to the number of doses left in the device, the tens digit needs only to be updated when the units digit changes from "0" to "9". Accordingly, a movement of the first counting member from its first relative position to its second relative position corresponds to an update of the first index element from displaying "0" to "9". This movement is transferred to the second counting member due to the engagement of the interaction element with the engagement elements. Accordingly, it corresponds to an update of the second index element displaying the tens digit of the second counted number. For example, the counted number may be updated from "20" to "19".

In one embodiment, the counting mechanism further comprises a blocking element preventing a further operation of the counting mechanism when the first counting member is in a pre-defined first relative blocking position with respect to the blocking element and the second counting member is in a pre-defined second relative blocking position with respect to the blocking element.

In particular, the blocking element may be enabled to prevent an operation of the drug delivery device when a given number of doses, in particular a predefined number of doses, has been delivered. The operation configured to be prevented by the blocking element may be a drug delivery operation of the drug delivery device.

Preferably, the operation is prevented permanently once the given number of doses has been delivered. In particular, once the blocking element has prevented the operation, the operation may only be allowed again if the housing of the device is opened and the blocking element is released. Preferably, a medicament container needs to be changed in order to unlock the blocking element. In this case, the device may be configured to be a reusable device allowing for a container change.

Alternatively, the device may be configured such that once the blocking element has locked the device, i.e. prevented the operation, it is not possible to enable the operation again at all. In this case, the device may be configured to be disposed once device has been locked.

In one embodiment, the first and the second counting member each comprises a passage. In particular, the passage may be defined in a plane perpendicular to the first rotation axis. Thus, the passage may be a passage, which permits an element to pass from the inside of the first or second counting member to outside of the first or second counting member in a direction which is oblique or perpendicular, preferably radial, with respect to the first or second rotation axis.

The passage may comprise an opening provided in the respective counting member, in particular a hole through the counting member. Preferably, the passage is provided in each counting member in a position different from the center of the counting member. Thereby, the position of the passage alters when the counting member rotates about the respective axis.

In one embodiment, the blocking position of the first counting member corresponds to the passage of the first counting member being aligned to the blocking element, and the blocking position of the second counting member corresponds to the passage of the second counting member being aligned to the blocking element.

In particular, the alignment of the passage of the first counting member to the blocking element is an alignment as seen in a plane perpendicular to the first rotation axis and in a direction perpendicular to the first rotation axis. Further, the alignment of the passage of the second counting member to the blocking element is an alignment as seen in a plane perpendicular to the second rotation axis and in a direction perpendicular to the second rotation axis.

In the blocking position of the counting mechanism, the passages are aligned with each other.

Preferably, the counting mechanism is configured such that the passages of the first and the second counting member and the blocking element are aligned when the given number of doses has been delivered and when the counting mechanism has counted the given number. The passages of the first and the second counting member may allow a movement of the blocking element, in particular a movement to a blocking position wherein the blocking element prevents a further operation of the counting mechanism. Moreover, in the blocking position, the blocking element may be configured and arranged to contact an interaction element of the drug delivery device which has to be moved during the operation and further the blocking element may be configured and arranged to prevent a movement of this element.

In one embodiment, the second counting member comprises a second interaction element, the counting mechanism further comprises a third counting member comprising third engagement elements that are enabled to engage with the second interaction element of the second counting member, the counting mechanism further comprises a second separating member, the second counting member is moveable relative to the second separating member to a first and a second relative position, and the second separating member is configured to prevent an engagement of the second interaction element with the third engagement elements when the second counting member is in its second relative position with respect to the second separating member.

Accordingly, the mechanism which is used to transfer a movement of the first counting member to the second counting member may also be used to transfer a movement of the second counting member into a movement of the third counting member. Moreover, the third counting member may further comprise an index element configured to display a hundreds digit of the counted number.

In one embodiment, a drug delivery device comprises the above-discussed counting mechanism.

The drug delivery device may be an inhaler, in particular a dry powder inhaler. However, the dose counting mechanism is also suitable for any other drug delivery device, e.g. an injector such as an injection pen. In particular, the dose counting mechanism may be used in a fixed-dose drug delivery device, i.e. a device in which the size of the drug which is delivered may not be varied by the user. Rather, in a fixed-dose device, the size of the dose is set by the design of the delivery mechanism.

DETAILED DESCRIPTION

Like elements, elements of the same kind and identically acting elements may be provided with the same reference numerals in the figures.

Figure 1:
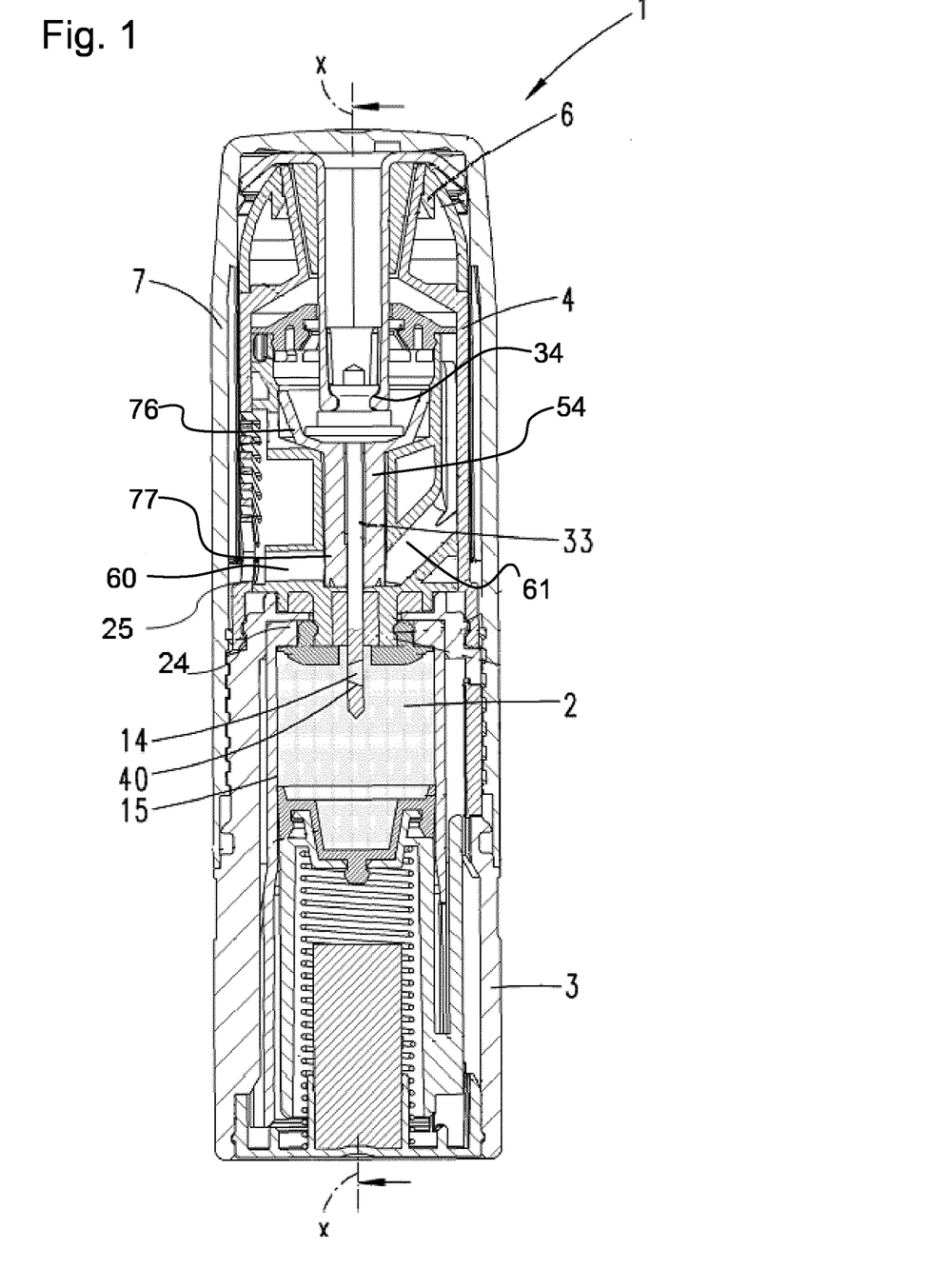
FIG. 1 schematically shows a sectional side view of an inhalation device.

In FIG. 1, a sectional side view of an inhalation device 1 is shown.

The inhalation device 1 comprises a housing 3. The device 1 comprises an outer cylinder 4. The outer cylinder 4 is secured against axial movement with respect to the housing 3. The outer cylinder 4 is rotatable with respect to the housing 3.

The inhalation device 1 further comprises a mouthpiece 6. The inhalation device 1 comprises a cap 7. The cap 7 is used for covering the mouthpiece 6. The cap 7 may comprise a thread, preferably a screw thread. The cap 7 may be rotatable with respect to the housing 3 for screwing the cap 7 onto the device 1 and for unscrewing the cap 7 from the device 1. The outer cylinder 4 is rotationally fixed to the cap 7. In particular, the outer cylinder 4 follows rotation of the cap 7 with respect to the housing 3. For the detailed description of the components of the inhalation device 1 and their mechanical cooperation it is referred to document WO 2009/065707 A1.

The device 1 comprises a storage chamber 15. The storage chamber 15 holds one dose, preferably a plurality of doses, of a medical substance 2. The substance 2 may be a powder.

In particular, the plurality of doses may correspond to a predefined number of doses, such that after the predefined number of doses has been delivered a lock-out mechanism may prevent a further operation of the device. The lock-out mechanism is not shown in FIG. 1, but will be discussed in detail later on.

A numerical value corresponding to the predefined number of doses is a starting value of a dose counting mechanism. Before the first dose delivery, the dose counting mechanism displays this predefined number as the number of available doses and with every dose delivery the number is decremented. Alternatively, the dose counting mechanism may display the number of doses that already have been delivered. In this case, the dose counting mechanism displays "0" as predefined number before the first dose delivery and with every dose delivery the number is incremented. The dose counting mechanism is not shown in FIG. 1, but the dose counting mechanism will be discussed in detail later on.

The storage chamber 15 is terminated by a chamber ceiling 24. The chamber sealing 24 is formed integrally with a top wall of the storage chamber 15. The device 1 further comprises a rotary part 25. The rotary part 25 is of substantially plate-like configuration and is connected in a rotationally fixed manner to the outer cylinder 4. Accordingly, the rotary part 25 follows rotation of the cap 7 and, hence, of the outer cylinder 4 about a main longitudinal axis x of the device 1 with respect to the storage chamber 15. However, the rotary body 25 is axially fixed relative to the housing 3.

The device 1 further comprises a metering rod 33. The metering rod 33 may be connected to the cap 7 by a snap fit element 34 when the cap 7 is engaged to the housing 3.

When the metering rod 33 is connected to cap 7 by the snap fit element 34 a rotation of the metering rod 33 relative to the cap 7, and thereby also relative to the rotary part 25, is prevented. Accordingly, the metering rod 33 follows rotational movement of the cap 7 and, hence, of the rotary part 25 about the main longitudinal axis x when the cap 7 is mounted onto the device 1 or demounted from the device 1.

When the cap 7 is re-engaged to the housing 3 the metering rod 33 travels axially in the proximal direction such that the most proximal part of the metering rod 33 comprising a metering chamber 40 enters the storage chamber 15. When the cap 7 is disengaged from the housing 3 the metering rod 33 travels axially in the distal direction such that the most proximal part of the metering rod 33 exits the storage chamber 15. In this context, "distal" may refer to the end of the inhalation device closest to the mouthpiece 6. Accordingly, "proximal" may refer to the end of the inhalation device furthest away from the mouthpiece 6.

In particular, the metering rod 33 is configured for functioning as a moving metering chamber 40 for a sub-quantity 14 of the substance 2 which is to be dispensed during a specific delivery action. The metering chamber 40 is formed in that end section of the metering rod 33 which projects into the substance 2.

The inhalation device 1 further comprises a flow path comprising a flow channel 60 and an intermediate channel portion 61.

The inhalation device 1 further comprises an actuating element 54. The actuating element 54 comprises a piston comprising tongues 77 and a piston head 76. The actuating element 54 has a first and a second position. The first position is more proximal than the second position. In the first position, the tongues 77 of the actuating element 54 block the flow path between the flow channel 60 and the intermediate channel portion 61. In its second position, the actuating element 54 is positioned more distally such that the tongues 77 do not block the flow path between the flow channel 60 and the intermediate channel portion 61 anymore.

The cap 7 is removed from the housing 3 by unscrewing the cap 7 from the housing 3. Accordingly, the cap 7 performs concurrently an axial movement in the distal direction and a rotational movement. The cap 7 and the rotary part 25 are in a splined engagement when the cap is attached to the housing 3. During disengagement of the cap 7 from the housing 3, the rotational movement of the cap 7 is transferred into a rotation of the rotary part 25 around the longitudinal axis x due to their splined engagement. The rotation of the rotary part 25 is transferred into a rotation of the actuation element 54. Further, the concurrent axial and rotational movement of the cap 7 is transferred to the metering rod 33 concurrently performing an axial movement in the distal direction and a rotational movement around the longitudinal axis x. As the cap 7 approaches the end of the threaded connection to the housing 3, the snap fit element 34 is disengaged from the metering rod 33.

During disengagement of the cap 7 from the housing 3, the actuating element 54 is not moved axially relative to the housing 3. Accordingly, the actuating element 54 is in its first position before and after disengagement of the cap 7 from the housing 3.

When the cap 7 is fully disengaged from the housing 3, the metering chamber 40 is in a first condition. The first condition of the metering chamber 40 is defined by the tongues 77 of the actuating element 54 closing the metering chamber 40 such that the metering chamber 40 is not in contact with the flow path. Accordingly, when the actuating element 54 is in its first position and the cap 7 is disengaged from the housing 3, the metering chamber 40 is in its first condition.

In the first condition of the metering chamber 40, the tongues 77 of the actuating element 54 cover the metering chamber 40 on each side. Accordingly, in this first condition, it is not possible for the sub-quantity 14 of substance to trickle out. Rather, the substance is reliably retained in the metering chamber 40.

After the cap 7 has been demounted, the user may trigger an inhalation operation by subjecting the device to a suction airstream, in the simplest case by the user breathing in. Air is sucked in via the mouthpiece 6, and this, in first instance, by virtue of the piston head 76 being subjected to the action of air, results in the actuating element 54 being displaced axially in the direction of the mouthpiece 6.

By virtue of the axially displaced actuating element 54, the tongues 77 are likewise displaced axially, in order to release the metering chamber 40. The metering chamber 40 is then in a second condition. The second condition of the metering chamber 40 is defined by the actuating element 54 being in its second position. In its second condition, the metering chamber 40 lies freely in a flow path between a flow channel 60 and an intermediate channel portion 61. The metering chamber is cleared out with air being sucked from the flow channel 60.

After the inhalation operation, the cap 7 may be engaged to the housing 3. During engagement of the cap 7 to the housing 3, the cap 7 is moved axially in the proximal direction and concurrently rotated around the longitudinal axis x. The snap fit element 34 engages to the metering rod 33 at the beginning of the threaded connection. Thereby the metering rod 33 is rotated and moved into the proximal direction when the cap 7 is engaged to the housing 3.

During reengagement of the cap 7 to the housing 3, the metering rod 33 is moved in a proximal direction due to the interaction with the cap 7. If the actuating element 54 is in its second position and the metering rod 33 is moved in the proximal direction, this movement is transferred to the actuating element 54. Thereby, the actuating element 54 is moved from its second position to its first position.

However, in case the cap 7 is disengaged from the housing 3 and afterwards reengaged to the housing 3 without a drug delivery being performed in between, the actuating element remains in its first position the whole time. Accordingly, as the actuating element 54 is already in its first position, it can not be moved axially during engagement of the cap 7 to the housing 3.

The inhalation device 1 further comprises a dose counting mechanism 5 and a lock-out mechanism which, for clarity reasons, are not depicted in FIG. 1. The dose counting mechanism 5 counts the number of doses left in the device 1. Alternatively, the counted number may correspond to another quantity, e.g. the number of doses having been delivered by the inhalation device 1.

Figure 2:
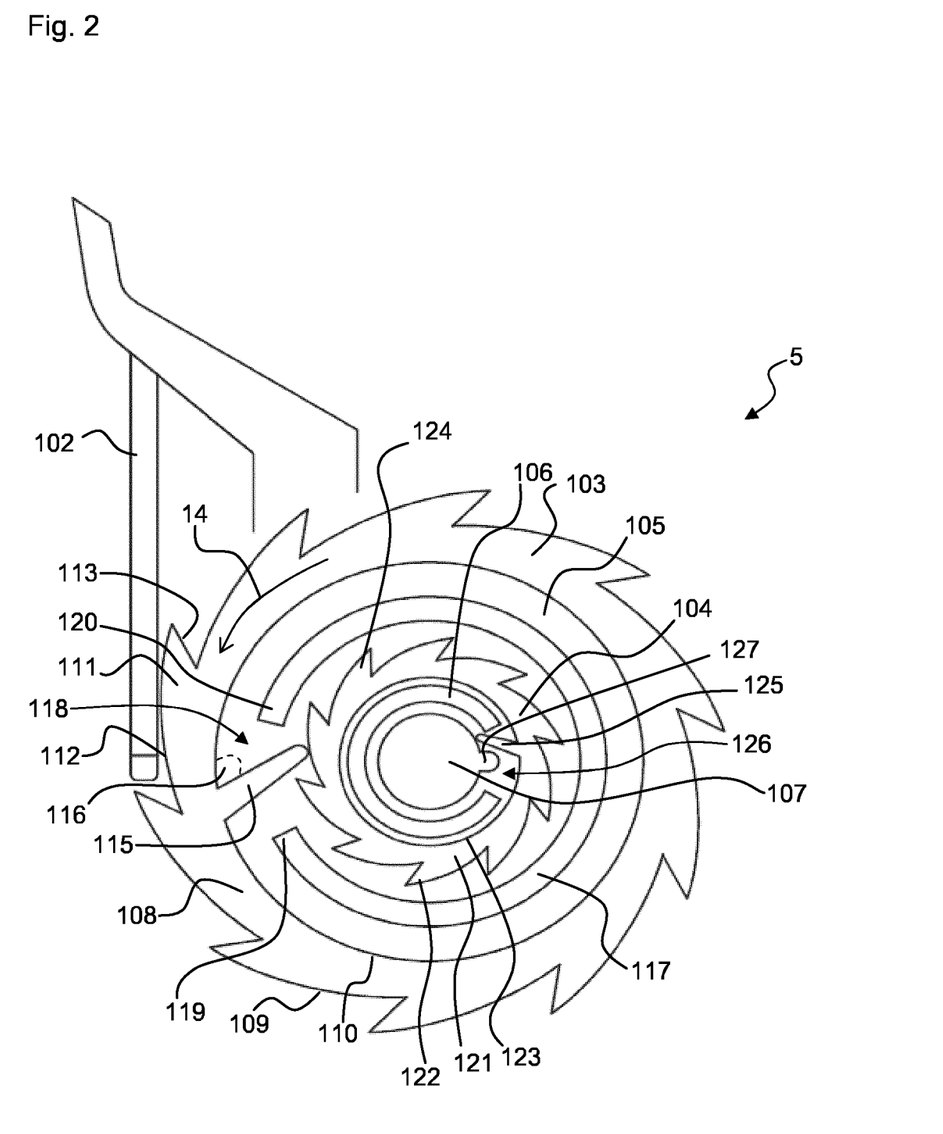
FIG. 2 shows a counting mechanism in a cross-sectional view wherein a first counting member is in a first position.

In FIG. 2, a cross-sectional view of a counting mechanism 5 for a drug delivery device is shown. The drug delivery device may be the inhalation device 1 shown in FIG. 1. Alternatively, the drug delivery device may be an injection pen, in particular a fixed-dose injection pen.

The drug delivery device comprises an interaction member 102. The interaction member may be coupled to the actuation element 54. The drug delivery device is configured such that the interaction member 102 is moved in a dose delivery operation. Further, the drug delivery device is configured such that the interaction member 102 is moved in an after dose delivery operation. In particular, in the dose delivery operation, the interaction member 102 is moved from a first axial position to a second axial position. In the after dose delivery operation, the interaction member 102 is moved from its second axial position to its first axial position.

In particular, the dose delivery operation may correspond to a suction carried out by a user. Therefore, the movement of the interaction member 102 may be triggered and expediently driven, preferably solely, by a user's suction airstream. Further, the after dose delivery operation may correspond to a re-engagement of the cap 7 to the housing 3. A counting is carried out only, if the dose delivery operation and subsequently the after dose delivery operation is carried out. In the present embodiment, a counting is carried out only, if a user performs a drug delivery operation is performed and if, subsequently, to the delivery operation the cap 7 is reengaged to the housing 3.

The user may perform a suction action for performing the dose delivery operation and the actuating element 54 is moved due to this suction action. The movement of the actuating element 54 requires a defined threshold vacuum which has to be overcome by a user, as, otherwise, the actuating element 54 would not move at all. When the actuating element 54 is moved, this movement permits the dose to be retrieved from the metering rod and dispersed in the suction airstream generated by the user. Consequently, the counting mechanism, the operation of which is linked to the movement of the actuating element 54 only operates, if the actuation element 54 was moved and the dose was released. Consequently, the counting mechanism 5 is a direct counting mechanism which counts only, if a suction airstream has reached the dose of drug provided in the metering rod. However, in some designs of the dose counting mechanism 5, to update the counting mechanism an after dose delivery operation, e.g. a reengagement of the cap 7 to the housing 3, may be required.

The counting mechanism 5 is configured to interact with the interaction member 102 of the drug delivery device. The counting mechanism 5 comprises a first counting member 103, a second counting member 104 and a first separating member 105. In the embodiment shown in FIG. 2, the counting mechanism 5 further comprises a second separating member 106 and a third counting member 107.

The first counting member 103 comprises a first main body 108. The first main body 108 has a tubular shape. The first main body 108 has an outer surface 109 and an inner surface 110. Further, the first counting member 103 comprises first engagement elements 111. The first engagement elements 111 are arranged at the outer surface 109 of the first main body 108. The first engagement elements 111 are protrusions, in particular teeth.

The interaction member 102 of the drug delivery device is enabled to interact with the first engagement elements 111 of the first counting member 103. In particular, in its first axial position, the interaction member 102 abuts a first face 112 of an engagement element 111 of the first counting member 103. The first axial position of the interaction member 102 corresponds to the actuating element 54 being in its first position such that it closes the metering chamber 40 and the metering chamber 40 is not in contact with the flow path.

When the interaction member 102 is moved from its first axial position to its second axial position, it slides along the first face 112 of the engagement element 111 and in its second axial position it abuts a second face 113 of the engagement element 111. The second axial position of the interaction member 102 corresponds to the actuating element 54 being in its second, more distal position wherein it does not block the flow path between the flow channel 60 and the intermediate channel portion 61 anymore such that a drug delivery is performed.

Further, when the interaction member 102 is moved from its second axial position back to its first axial position, it remains in abutment with the second face 113 of the engagement element 111 at least during a first part of said movement and, thereby, it exerts a force on the second face 113 of the engagement element 111. This force results in a rotation of the first counting member 103. As described in more detail later on, this rotation corresponds to an incrementing or decrementing of the number counted by the counting mechanism 5.

However, if the actuating element 54 is not moved, e.g. if the cap 7 is disengaged from the housing 3 and afterwards reengaged to the housing 3, the interaction member 102 is not moved as well. Accordingly, no movement is transferred to the counting mechanism. In other words, if an after dose delivery operation is performed without a dose delivery operation being performed beforehand, the dose counting mechanism 5 is not updated, i.e. the counted number is not incremented or decremented.

The first counting member 103 is mounted such that it can rotate around a first rotation axis in a first rotation direction 114. The interaction member 102 is movable axially, particularly in a direction perpendicular to the rotation axis. Accordingly, the engagement elements 111 of the first counting member 103 may be arranged such that the interaction member 102 is enabled to exert a force on the engagement elements 111 perpendicular to the rotation axis.

Moreover, the first counting member 103 comprises an interaction element 115. The interaction element 115 is a projection, in particular a cam. The interaction element 115 is enabled to interact with the second counting member 104. The interaction element 115 is arranged at the inner surface 110 of the first main body 108 of the first counting member 103.

The interaction element 115 is elastically deformable. If no force is applied to the interaction element 115, it protrudes from the inner surface 110 of the first main body 108 to an extent sufficient to cooperate with one of the engagement elements 111. The interaction element 115 and the inner surface 110 of the main body 108 arranged behind the interaction element 115, as seen in the first rotation direction 114, define an acute angle 116.

Moreover, the counting mechanism 1 comprises the first separating member 105. The separating member 105 comprises a wall 17 that is continuous and that provides one opening 118. In particular, the wall 117 comprises at least one opening 118 for each interaction element 115 of the first counting member 103. The opening 118 in the wall 117 is bound by a first and a second edge 119, 120.

The size of the opening 118 is chosen such that it is big enough for the interaction element 115 to pass through the opening 118. The first counting member 103 is movable relative to the first separating member 105. In particular, the first counting member 103 is rotatable around the first rotation axis relative to the first separating member 105. The first counting member 103 is rotatable at least between a first and a second relative position with respect to the separating member 105.

In particular, the first counting member 103 is rotatable to ten pre-defined positions relative to the first separating member 105. Each of said positions may be space equidistantly, i.e. by a pre-determined angle, from the respective previous position. In particular, said angles correspond to a tenth of a complete rotation of 360°.

One of the ten predefined positions is a first position wherein the opening 118 allows the interaction element 115 to engage one of the engagement elements 111. The other nine of the ten predefined positions are second positions wherein an engagement of the interaction element 115 with the engagement elements 111 is prevented. In particular, the interaction element 115 is enabled to interact with the second counting member 104 in the first position. The interaction element 115 is prevented from interacting with the second counting member 104 in each of the second to tenth position by the wall 117.

Figure 3:
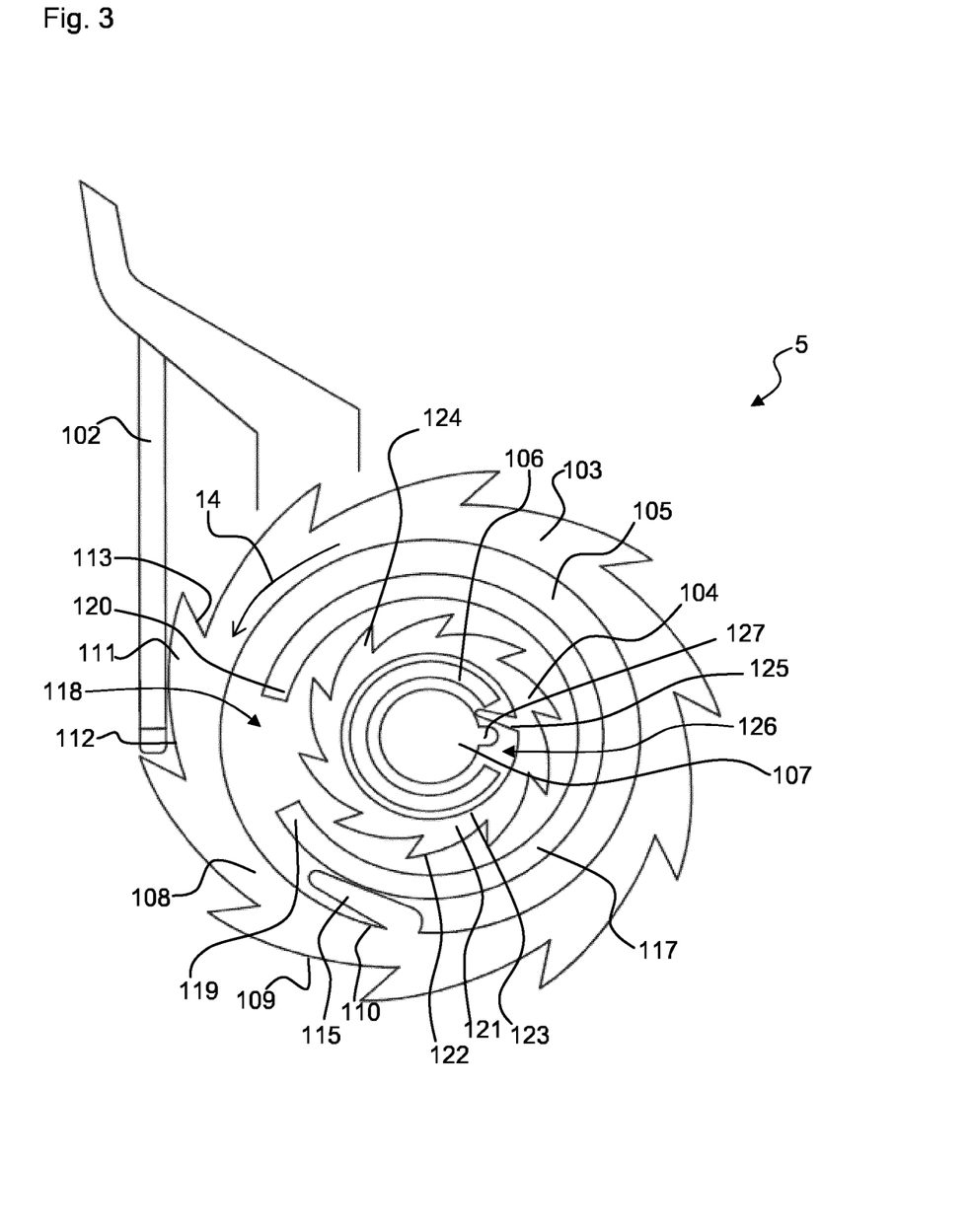
FIG. 3 shows the counting mechanism of FIG. 2 in a cross-sectional view wherein the first counting member is in a second position.

FIG. 2 shows the first counting member 103 in its first position relative to the first separating member 105. FIG. 3 shows the first counting member in its second position relative to the first separating member 105.

In the first position, the interaction element 115 and the opening 118 defined by the first separating member 105 are aligned in a direction perpendicular to the first rotation axis, as seen in a plane perpendicular to the first rotation axis. Accordingly, the interaction element 115 passes through the opening 118 and engages with the second counting member 104.

However, after a dose delivery operation and an after dose delivery operation of the drug delivery device has been performed, the first counting member 103 is moved from its first rotational position to its second rotational position relative to the first separating member 105. During this rotation, the interaction element 115 is brought in abutment with the first edge 119 of the opening 118 defined in the separating member 105. The separating member 105 exerts a force on the interaction element 115 in a direction away from the first rotation axis. In the second relative position, the interaction element 115 is elastically deformed. In particular, the interaction element 115 is bent in a direction away from the rotation axis when moving from the first to the second position.

The second counting member 104 comprises a second main body 121. The second main body 121 has a tubular shape. The first main body 108 of the first counting member 103 is arranged on one side of the wall 117 of the first separating member 105 and the second main body 121 of the second counting member 104 is arranged on the other side of the wall 117. Only the interaction element 115 is enabled to pass through the opening 118 defined in the wall 117.

The second main body 121 comprises an outer surface 122 and an inner surface 23. Further, the second counting member 104 comprises engagement elements 124. The engagement elements 124 of the second counting member 104 are protrusions, in particular teeth. The engagement elements 124 of the second counting member 104 are arranged at the outer surface 122 of the second main body 121.

The first main body 108 and the second main body 121 are tubular shaped having different radiuses. In particular, the second main body 121 is arranged inside the first main body 108, preferably as seen in a plane perpendicular to the first rotation axis. However, in an alternative embodiment, the first main body 108 may be arranged inside the second main body 121.

The second counting member 104 is moveable relative to the first separating member 105. The second counting member is enabled to rotate around a second rotation axis. The second rotation axis is parallel, in particular identical, to the first rotation axis.

Further, the second counting member 104 and the first counting member 103 are movable relative to each other when the interaction element 115 is not engaged to the engagement elements 124 of the second counting member 104. If the interaction element 115 engages one of the engagement elements 124 of the second counting member 104, a movement, in particular a rotation, of the first counting member 103 triggers a movement, in particular a rotation in the first rotational direction, of the second counting member 104.

The material of the interaction element 115 is chosen such that it is deformed when the first counting member 103 rotates and it abuts the first edge 119 of the opening 118 defined in the first separating member 105. At the same time, the material is stiff enough such that the interaction element 115 can exert a force on the second counting member 104, in particular the engagement elements 124 of the second counting member 104, without being deformed significantly. Consequently, a rotation of the first counting member 103 may be transferred to the second counting member 104.

A mechanism of the same construction is used to transfer a movement of the second counting member 104 to a movement of a third counting member 107. In particular, the second main body 121 of the second counting member 104 comprises a second interaction element 125. The third counting member 107 comprises a third main body 134 comprising the engagement element 127. Further, the second separating member 6 defines a second opening 26. When the opening 26 defined in the second separating member 6 is aligned to the second interaction element 125 defined by the second counting member 104 in a direction perpendicular to the second rotation axis, the second interaction element 125 engages to engagement elements 127 of the third counting member 107.

The second counting member 104 also has ten defined relative rotational position with respect to the second separating member 106. In each of the second to the tenth rotational position, the second opening 126 defined by the second separating member 106 is not aligned to the second interaction element 125 of the second counting member 104. Accordingly, the second interaction element 125 is prevented from engaging the engagement elements 127 of the third counting member 107. In the first rotational position, the second opening 126 of the second separating member 106 is aligned to the second interaction element 125 of the second counting member 104 in a direction perpendicular to the second rotation axis. Then, the second interaction element 125 is enabled to engage with one of the engagement elements 127 of the third counting member 107. Accordingly, a rotation of the second counting member 104 from its first rotational position to its second rotational position with respect to the second separating member 106 is transferred to a rotation of the third counting member 107.

Figure 4:
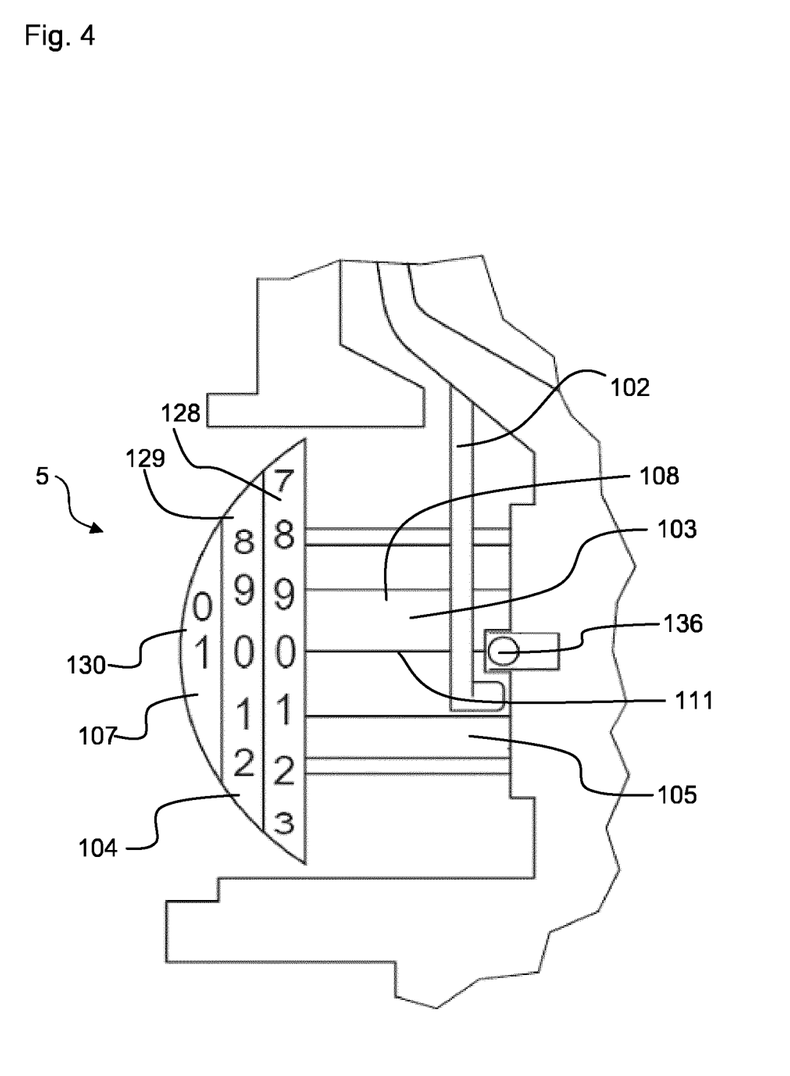
FIG. 4 shows the counting mechanism in a perspective view.
Figure 5:
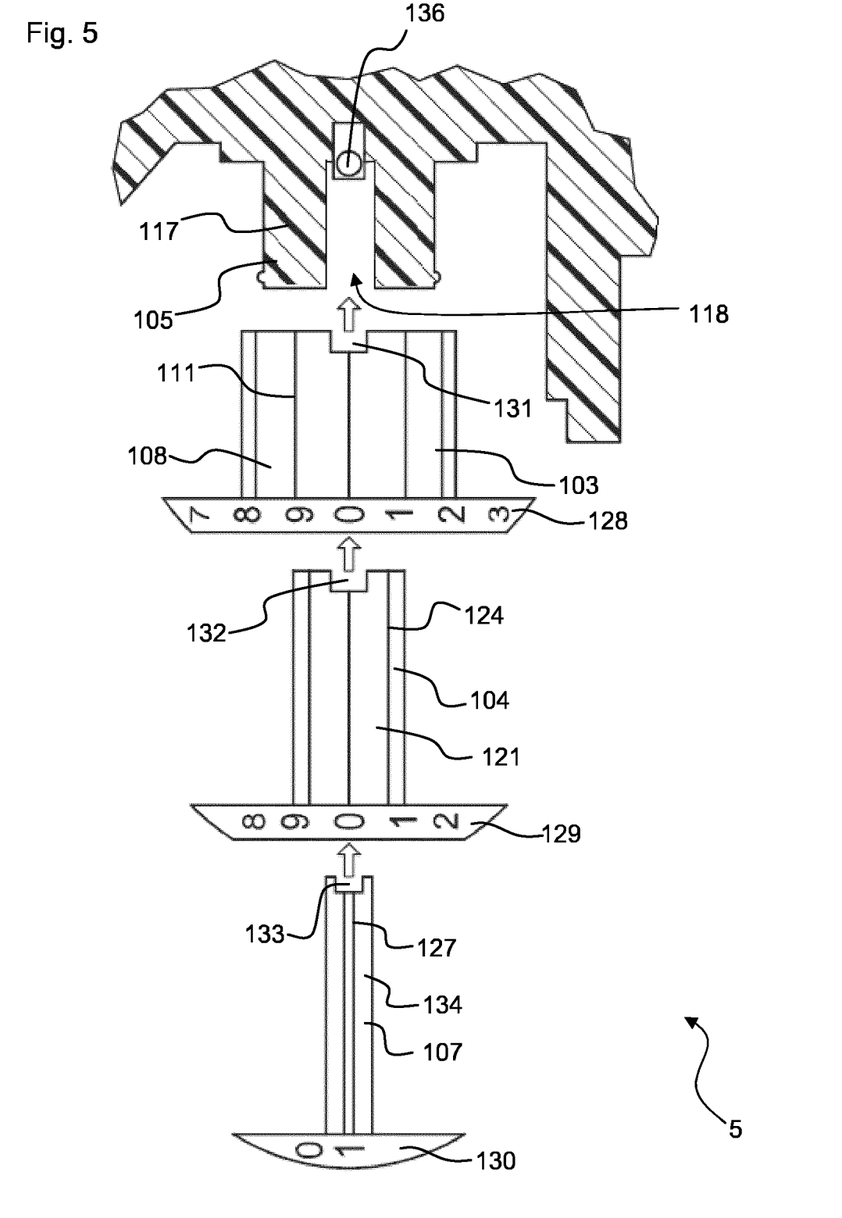
FIG. 5 shows the counting mechanism in an exploded view.

FIG. 4 shows the counting mechanism 5 in a perspective view. FIG. 5 shows the counting mechanism 5 in an exploded view.

Further, it can be gathered from FIGS. 4 and 5 that the first counting member 103 comprises a first index element 128. Digits ranging from "0" to "9" are arranged on the first index element 128. Moreover, the second counting member 104 comprises a second index element 129 and the third counting member 107 comprises a third index element 130 wherein digits are arranged on each of the second and third index elements 129, 130.

As seen in a direction along the first rotation axis, the first counting member 103 comprises a tubular shaped main body 108 and adjacent to the main body 108 and, preferably, in direct mechanical contact to the first main body 108, the first index element 128. The first index element 128 is fixed to the first main body 108 such that it follows every movement of the first main body 128. The first index element 128 has a larger width than the first main body 108, preferably as seen in a direction perpendicular to the first rotation axis.

Further, as seen in a direction along the first rotation axis, the second counting member 104 comprises a tubular shaped main body 121 and adjacent to the main body 121 and in direct mechanical contact to the second main body 121, the second index element 129. The second index element 129 is fixed to the second main body 121 such that it follows every movement of the second main body 121. The second index element 129 has a larger width than the second main body 121, preferably as seen in a direction perpendicular to the first rotation axis. Further, the second index element 129 has a smaller width than the first index element 128, preferably as seen in a direction perpendicular to the first rotation axis.

Furthermore, as seen in a direction along the first rotation axis, the third counting member 107 comprises a tubular shaped main body 134 and adjacent to the main body 134 and in direct mechanical contact to the third main body 134, the third index element 130. The third index element 130 is fixed to the third main body 134 such that it follows every movement of the third main body 134. The third index element 130 has a larger width than the third main body 134, preferably as seen in a direction perpendicular to the first rotation axis. Further, the third index element 130 has a smaller width than the first index element 128 and the second index element 129, preferably as seen in a direction perpendicular to the first rotation axis.

Moreover, the first main body 108 has a smaller extent along the first rotation axis than the second main body 121. Therefore, the second index element 129 is arranged above the first index element 128 as seen in a direction along the first rotation axis. Further, the second main body 121 has a smaller extend along the first rotation axis than the third main body 134. Therefore, the third index element 130 is arranged above the second index element 129 as seen in a direction along the first rotation axis.

The first, the second and the third index elements 128, 129, 130 of the first, the second and the third counting member 103, 104, 107 are configured to cooperate to display a counted number. In particular, the drug delivery device may comprise a window. The index elements 128, 129, 130 are arranged such that one digit of each index element 128, 129, 130 is visible through the window. Accordingly, a counted number is formed by the three digits visible in the window. The counted number may correspond to the number of doses left in the device. Alternatively, the counted number may correspond to the number of drug delivery operations that have already been carried out by the drug delivery device.

The digit displayed by the first index element 128 of the first counting member 103 corresponds to the unit digit of the counted number. The digit displayed by the second index element 129 of the second counting member 104 corresponds to the tens digit of the counted number. Moreover, the digit displayed by the third index element 130 of the third counting member 107 corresponds to the hundreds digit of the counted number. If the drug delivery device is enabled to deliver a maximum number of doses lower than 200, it is sufficient for the third index element 130 to comprise the digits "0" and "1".

The counting mechanism 5 is configured such that, after disengagement of the interaction element 115 of the first counting member 103 from one of the engagement elements 124 of the second counting member 104, the first counting member 103 carries out nine tenth of a complete rotation until the interaction element 115 of the first counting member 103 is enabled to engage to another engagement element 124 of the second counting member 104. A complete rotation of the first counting member 103 corresponds to the digits "9" to "0" of the first index element 128 being visible in the window successively.

After a complete rotation of the first counting member 103, the interaction element 115 of the first counting member 103 engages with the next engagement element 124 of the second counting member 104. If the first counting member 103 is now rotated by the pre-determined angle, this rotation transfers into a rotation of the second counting member 104. Accordingly, the second index element 129 of the second counting member 104 is rotated by the pre-determined angle and the digit of the second index element 129 visible in the window is altered.

Further, the first counting member 103 comprises a first passage 131. The second counting member 104 comprises a second passage 132. The third counting 6 member comprises a third passage 133. Each of the passages 131, 132, 133 is arranged in the main body 108, 121, 134 of the respective counting member 103, 104, 107.

Moreover, the counting mechanism 5 further comprises a blocking element 136. The blocking element 136 is a pin, for example. The blocking element 136 comprises a blocking position and an non-blocking position with respect to each counting member 103, 104, 107.

The blocking element 136 is biased, i.e. by a spring. As seen in a radial direction pointing away from the first rotation axis, the blocking element 136 is arranged inside the counting members 103, 104, 107 in the non-blocking position. The blocking element 136 is enabled to move in a direction perpendicular to the first rotation axis and away from the first rotation axis.

The position of the blocking element 136 closest to the first rotation axis is an non-blocking position with respect to each of the first, second and third counting member 103, 104, 107.

When the third passage 133 defined in the main body 134 of the third counting member 107 is aligned with the blocking element 136, the blocking element 136 is enabled to pass through the passage 133. Thereby, the blocking element 136 blocks any further movement of the third counting member 107. However, in this position, the blocking element 136 does not block movements of the second or the first counting member 103, 104. Accordingly, the blocking element 136 is in a blocking position for the third counting member 107 and in an non-blocking position for the first and second counting member 103, 104.

When the blocking element 136 is in a blocking position with respect to the third counting member 107 and the second passage 132 defined in the second counting member 104 is aligned to the blocking element 136, the blocking element 136 passes through this passage 132 and blocks any further movements of the second counting member 104. Accordingly, the blocking element 136 is then in a blocking position for the second and third counting member 103, 104 and in an non-blocking position for the first counting member 103.

When the blocking element 136 is in a blocking position with respect to the second and third counting member 103, 104 and the first passage 131 defined in the first counting member 103 is aligned to the blocking element 136, the blocking element 136 passes through this passage 131 and blocks any further movements of the first counting member 103, thereby blocking any further movement of any of the counting members 103, 104, 107 of the counting mechanism 5. Accordingly, the blocking element 136 is then in a blocking position for each of the first, second and third counting member 103, 104, 107.

Moreover, the blocking element 136 may be enabled to engage with the interaction member 102 of the drug delivery device, when the counting mechanism 5 is blocked. Thereby, the blocking element 136 is enabled to block any movements of the interaction element 102 and to prevent dose delivery operations.

Alternatively or additionally, the blocking element 136 may prevent any further movement of the counting members 103, 104, 107 in its blocking position. Accordingly, if the counting members 103, 104, 107 are prevented from moving, it is no longer possible to reengage a cap 7 to the housing 3 as this would require a proximal movement of the interaction member 102. However, such a movement is prevented if the counting members 103, 104 107 are fixed, such that they cannot perform a rotation anymore.

The term "drug", as used herein may mean a pharmaceutical formulation containing at least one pharmaceutically active compound, for example for the treatment of obstructive airway or lung diseases such as asthma or chronic obstructive pulmonary disease (COPD), local respiratory tract oedema, inflammation, viral, bacterial, mycotic or other infection, allergies, diabetes mellitus.

The active pharmaceutical compound is preferably selected from the group consisting of active pharmaceutical compounds suitable for inhalation, preferably antiallergenic, antihistamine, anti-inflammatory, antitussive agents, bronchodilators, anticholinergic drugs, and combinations thereof.

The active pharmaceutical compound may for example be chosen from:

an insulin such as human insulin, e.g. a recombinant human insulin, or a human insulin analogue or derivative, a glucagon-like peptide (GLP-1) or an analogue or derivative thereof, or exendin-3 or exendin-4 or an analogue or derivative of exendin-3 or exendin-4;

an adrenergic agent such as a short acting β2-agonists (e.g. Salbutamol, Albuterol, Levosalbutamol, Fenoterol, Terbutaline, Pirbuterol, Procaterol, Bitolterol, Rimiterol, Carbuterol, Tulobuterol, Reproterol), a long acting β2-agonist (LABA, e.g. Arformoterol, Bambuterol, Clenbuterol, Formoterol, Salmeterol), an ultra LABA (e.g. Indacaterol) or another adrenergic agent (e.g. Epinephrine, Hexoprenaline, Isoprenaline (Isoproterenol), Orciprenaline (Metaproterenol));

a glucocorticoid (e.g. Beclometasone, Budesonide, Ciclesonide, Fluticasone, Mometasone, Flunisolide, Betamethasone, Triamcinolone);

an anticholinergic agent or muscarinic antagonist (e.g. Ipratropium bromide, Oxitropium bromide, Tiotropium bromide);

a mast cell stabilizer (e.g. Cromoglicate, Nedocromil);

a xanthine derivative (e.g. Doxofylline, Enprofylline, Theobromine, Theophylline, Aminophylline, Choline theophyllinate);

an eicosanoid inhibitor, such as a leukotriene antagonist (e.g. Montelukast, Pranlukast, Zafirlukast), a lipoxygenase inhibitor (e.g. Zileuton) or a thromboxane receptor antagonist (e.g. Ramatroban, Seratrodast);

a phosphodiesterase type-4 inhibitor (e.g. Roflumilast);

an antihistamine (e.g. Loratadine, Desloratadine, Cetirizen, Levocetirizine, Fexofenadine);

an allergen immunotherapy (e.g. Omalizumab);

a mucolytic (e.g. Carbocisteine, Erdosteine, Mecysteine); an antibiotic or antimycotic;

or a combination of any two, three or more of the above-mentioned compound classes or compounds (e.g. Budesonide/Formoterol, Fluticasone/Salmeterol, Ipratropium bromide/Salbutamol, Mometasone/Formoterol);

or a pharmaceutically acceptable salt or solvate or esters of any of the above named compounds.

Pharmaceutically acceptable salts are for example acid addition salts and basic salts. Acid addition salts are e.g. a chloride, bromide, iodide, nitrate, carbonate, sulfate, methylsulfate, phosphate, acetate, benzoate, benzenesulfonate, fumarate, malonate, tartrate, succinate, citrate, lactate, gluconate, glutamate, edetate, mesylate, pamoate, pantothenate or a hydroxy-naphthoate salt. Basic salts are for example salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology. Pharmaceutically acceptable ester may for example be acetates, propionates, phosphates, succinates or etabonates.

Pharmaceutically acceptable solvates are for example hydrates.

The invention claimed is:

1. Counting mechanism for a drug delivery device, comprising a first counting member comprising an interaction element, a second counting member comprising engagement elements that are configured to engage with the interaction element of the first counting member, and a separating member, wherein the first counting member is moveable relative to the separating member between a first and a second relative position, and the separating member is configured to prevent an engagement of the interaction element with the engagement elements when the first counting member is in the second relative position with respect to the separating member, wherein the counting mechanism comprises a blocking element preventing a further operation of the counting mechanism when the first counting member is in a pre-defined first relative blocking position with respect to the blocking element and the second counting member is in a pre-defined second relative blocking position with respect to the blocking element.

2. Counting mechanism according to claim 1, wherein the separating member is configured to enable an engagement of the interaction element with one of the engagement elements when the first counting member is in the first relative position.

3. Counting mechanism according to claim 1, wherein the first counting member is moveable relative to the second counting member when the first counting member is in the second relative position.

4. Counting mechanism according to claim 1, wherein a movement of the second counting member is triggered by a movement of the first counting member when the first counting member is in the first relative position with respect to the separating member.

5. Counting mechanism according to claim 1, wherein the interaction element is elastically deformable.

6. Counting mechanism according to claim 1, wherein the first counting member is rotatable around a first rotation axis relative to the separating member.

7. Counting mechanism according to claim 6, wherein the second counting member is rotatable around a second rotation axis relative to the separating member and wherein the second rotation axis runs along the first rotation axis.

8. Counting mechanism according to claim 1, wherein the separating member comprises a wall provided with an opening.

9. Counting mechanism according to claim 8, wherein the interaction element protrudes through the opening in the wall in the first relative position of the first counting member with respect to the separating member.

10. Counting mechanism according to claim 8, wherein the interaction element abuts the wall in the second relative position of the first counting member with respect to the separating member.

11. Counting mechanism according to claim 1, wherein the first counting member comprises a first index element, the second counting member comprises a second index element, and the first and the second index element are configured to cooperate to display a number.

12. Counting mechanism according to claim 1, wherein the first and the second counting member each comprises a passage, and wherein the blocking position of the first counting member corresponds to the passage of the first counting member being aligned with the blocking element, and the blocking position of the second counting member corresponds to the passage of the second counting member being aligned with the blocking element.

13. Counting mechanism according to claim 1, wherein the second counting member comprises a second interaction element, the counting mechanism further comprises a third counting member comprising third engagement elements that are configured to engage with the second interaction element of the second counting member, the counting mechanism further comprises a second separating member, the second counting member is moveable relative to the second separating member between a first and a second relative position, and the second separating member is configured to prevent an engagement of the second interaction element with the third engagement elements when the second counting member is in its second relative position with respect to the second separating member.

14. Drug delivery device comprising a counting mechanism according to claim 1.

* * * * *